United States Patent [19]

Christen et al.

[11] 4,352,099
[45] Sep. 28, 1982

[54] GAS SENSING UNIT FOR USE IN ENVIRONMENT COMPRISING EXPLOSIVE GASES

[75] Inventors: Peter Christen, Männedorf; Hansheinrich Brändli, Uster; Bernhard Durrer, Stäfa; Arnim Sauerbrey, Adetswil, all of Switzerland

[73] Assignee: Cerberus AG, Männedorf, Switzerland

[21] Appl. No.: 128,529

[22] Filed: Mar. 10, 1980

[30] Foreign Application Priority Data

Mar. 16, 1979 [CH] Switzerland .......................... 2482/79

[51] Int. Cl.$^3$ .............................................. G08B 17/10
[52] U.S. Cl. ....................................... 340/633; 422/96
[58] Field of Search ....................... 340/632, 633, 634; 422/94, 95, 96, 97

[56] References Cited

U.S. PATENT DOCUMENTS

| | | | |
|---|---|---|---|
| 1,224,321 | 5/1917 | Philip et al. | 422/96 |
| 2,279,397 | 4/1942 | Hartline | 422/96 |
| 3,041,590 | 6/1962 | Lueci | 422/94 X |
| 3,117,843 | 1/1964 | Baker | 422/96 |
| 3,251,654 | 5/1966 | Palmer | 340/633 X |
| 3,421,362 | 1/1969 | Schaeffer | 422/94 X |
| 3,771,960 | 11/1973 | Kim et al. | 422/96 X |
| 3,964,036 | 6/1976 | Adachi et al. | 340/629 X |
| 3,989,463 | 11/1976 | Klein et al. | 340/634 X |
| 4,045,729 | 8/1977 | Loh | 340/634 X |

*Primary Examiner*—John W. Caldwell, Sr.
*Assistant Examiner*—Daniel Myer
*Attorney, Agent, or Firm*—Werner W. Kleeman

[57] ABSTRACT

A gas sensing unit designed to be protected against explosions and serving for the detection of combustible gases in an atmosphere, containing a gas sensor functioning according to the principle of catalytic oxidation or a semiconductor gas sensor. The gas sensing unit contains, within a housing, at least two mutually separated chambers or spaces. The one chamber is a compression-proof space and contains an electronic evaluation circuit for the gas sensor, the other chamber, which is a space structured to be protected against explosions, contains the gas sensor and a balancing element and is separated from the atmosphere by a sintered metal bushing or sleeve. A third explosion-proof chamber or space can be provided in the gas sensing unit for the purpose of connecting the lines or conductors. The gas sensor together with the balancing adapter forms an assembly or unit which can be pluggably arranged in the cover of the chamber containing the electronic system or hardware. With such type gas sensing unit it is possible to easily exchange the gas sensor at its erection site, without the need for having to open the compression-proof chamber containing the electronic components. The testing and balancing of the gas sensor can be accomplished at the manufacturing plant.

12 Claims, 8 Drawing Figures

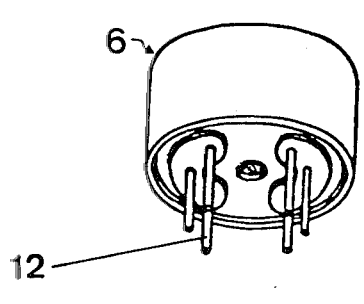
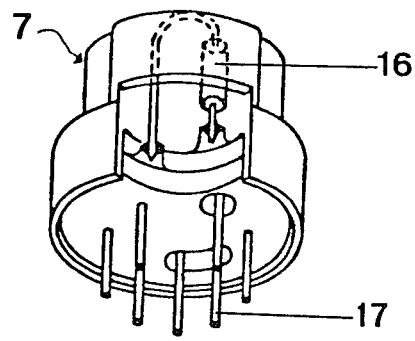
Fig. 2a  Fig. 2b
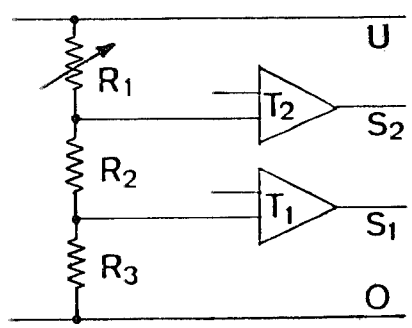
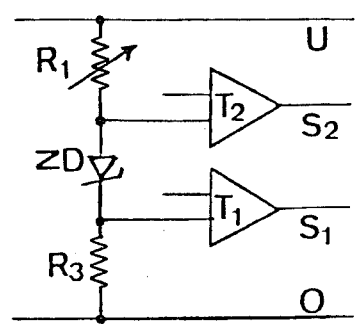
Fig. 3a  Fig. 3b
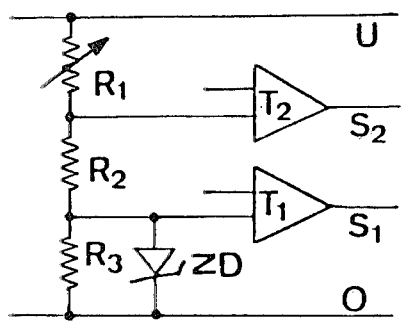
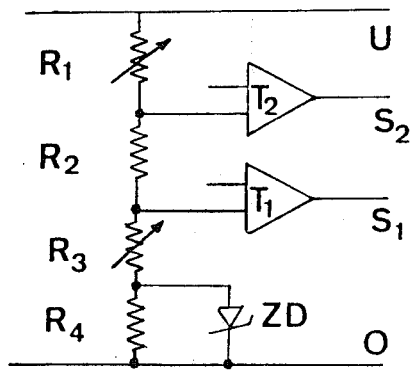
Fig. 3c  Fig. 3d

GAS SENSING UNIT FOR USE IN ENVIRONMENT COMPRISING EXPLOSIVE GASES

CROSS-REFERENCE TO RELATED CASE

This application is related to the commonly assigned U.S. application Ser. No. 54,786, filed July 5, 1979, and entitled "Gas Sensing Signaling System".

BACKGROUND OF THE INVENTION

The present invention relates to a new and improved construction of a gas sensing unit for use in environments containing explosive gases, which is operatively connected with a central station to thereby form a gas sensing signaling system. The gas sensing unit contains a gas sensor which, when exposed to the action of reduction gases, alters its electrical resistance.

In order to protect industrial plants or installations, pipe conduit channels, chemical storage areas and so forth against fires and also human beings from exposure to toxic gases, it is desirable to be able to detect at an incipient stage dangerous concentrations of combustible or noxious gases. In response to such detection it is then possible to initiate suitable counter measures, for instance shutting down operating installations which are improperly functioning, closing off leaking pipe conduits, starting ventilators or other exhaust apparatus, opening emergency exits and otherwise signaling to the occupants or personnel the need to leave the area and so forth, and in this way avoiding fires, explosions, toxic effects to the occupants or personnel and other damage.

In order to detect undesired and dangerous concentrations of reducing, i.e. oxidizable or combustible gases, there are known to the art gas sensing signaling or alarm systems composed of gas sensing units which are connected with a central station.

Also known to the art are gas warning equipment containing a diffusion measuring head equipped with active and inactive gas trace elements arranged in a mechanically easily detachable gas trace element insert below a cover plate formed of a gas pervious sintered or powdered metal. These gas warning devices generally use a gas detector-bridge circuit, wherein two electrically heated thermoelements are appropriately connected in circuit with one another, one thermoelement constituting a catalytically active thermoelement and the other an inactive thermoelement.

There are also known to the art gas warning devices containing as the gas sensor or gas sensing element metal oxide semiconductors, which when exposed to the action of reducing gases alter their electrical resistance. This resistance change is converted in an evaluation circuit into an electrical signal, by means of which there is activated the alarm device and there are initiated counter measures.

Representative gas sensing units are disclosed in U.S. Pat. No. 3,245,067, German Pat. No. 2,625,891 and the prior art referred to in the aforementioned copending U.S. application Ser. No. 054,786.

Since the working temperature of the gas sensors or gas sensing elements usually is in a temperature range where there has already been vastly exceeded the ignition temperature of the gases to be detected—for instance 180° C. for ether and acetaldehyde, 220° to 300° C. for gasoline and diesel fuels, 305° C. for acetylene and so forth—, it is necessary that measures be carried out which prevent that the gas warning devices cause ignition of the gases against whose presence there must be warned. For this purpose proposals have already been made to provide the gas sensors or gas sensing elements with a flame barrier formed of a small wire mesh or a grid. These flame barriers are suitable as a firedamp protection, but however provide no effective protection against explosions.

Furthermore, it has been proposed to arrange, within the region or area to be monitored, only the diffusion measuring head which is designed so as to be protected against explosions and to separately mount in relation thereto the evaluation circuit.

The utilization of semiconductors as gas sensors or gas sensing elements in gas warning devices is relatively new. The first usable semiconductor gas sensors became known to the art only at the start of the last decade, and significant in this respect are, by way of example, German Patent Publication Nos. 2,005,497 and 2,016,388. An appreciable drawback of the gas sensing elements or gas sensors which have been employed resides in the fact that, within a production or manufacturing series, there prevail great sensitivity differences, i.e. the resistance change as a function of the gas concentration is not the same for the individual gas sensors. In order to attain a positive giving or sounding of an alarm, it is therefore necessary that the evaluation circuit contains circuit components which enable balancing or compensating the aforementioned differences.

Since, on the other hand, the longevity or service life of the gas sensors or gas sensing elements is limited, it is necessary that they be checked at certain time intervals and, as the situation requires, exchanged. Consequently, the balancing or compensation operation needed of the gas sensors must be performed at the site of erection or employment. To this end the gas sensor must be brought into contact with an atmosphere containing a certain concentration of testing gas and humidity, whereas at the same time the evaluation circuit must be balanced. Since the evaluation circuit for the individual gas sensing units is located at the central station, the balancing operation for the individual gas sensors or gas sensing elements must be undertaken at this location, which, in turn, is associated with appreciable drawbacks as will be readily evident. This technique generally requires a second maintenance or service operator; with great distances between the gas sensing unit and the central station their prevail additional difficulties in communication between these two locations.

A further appreciable limitation of the heretofore known gas warning devices resides in the fact that the sensors must be accommmodated, at the site of erection or use, by means of a calibration gas to the electronic system. The calibration gases which can be obtained commercially are only present in a dry state in the transport flasks or containers for physical reasons. If, however, a dry gas is used for calibration purposes, then the sensors are appreciably less sensitive. To accomplish a correct balancing operation it is therefore necessary to moisten the test gas, so that there can be established conditions which are as close as possible to those encountered in practice. A really correct balancing, with reproducible conditions, is only therefore possible at the manufacturing plant. Yet, adjustment or balancing at the manufacturing plant was not at all possible with the heretofore prior art constructions of gas warning equipment, since the length of the lines between the gas sensor or gas sensing element and the central station is not exactly known, but however must be taken into account during balancing of the gas warning equipment.

It would have been obvious to accommodate both the evaluation circuit and the gas sensor within the same housing, i.e. to provide a gas sensing unit containing both the gas sensing element and evaluation circuit, and to bring the entire gas sensing unit to the factory in order to check and exchange, when necessary, the gas sensors or gas sensing elements. However, this likewise is associated with appreciable disadvantages. Due to the requirement of explosion safety the gas sensing units would be relatively large in design and cumbersome to handle. Additionally, the explosion-proof property of the gas sensing unit would be extremely difficult to realize and check. The evaluation circuit would be exposed to the ambient air, which would not be a tolerable state when the atmosphere is corrosive. With this type of construction the gas sensor only could be exchanged when the evaluation circuit is exposed or opened, so that there would prevail the danger of damaging and misadjustment thereof. Already with the slightest damage there no longer would have been correct the permissible tolerances for the explosion gaps, with the result that the explosion protection would no longer be present.

A further drawback would reside in the fact that explosion protected, i.e. compression-proof chambers or spaces can only be opened with difficulty, and these difficulties increase the larger the size of such chambers or spaces. An appreciable shortcoming also resides in the fact that the exchange of the gas sensing unit at its erection site is quite cumbersome, since it is also necessary that the electrical connections of the gas sensing unit with the line network be carried out in an explosion protected design, i.e. would be difficult to solve.

SUMMARY OF THE INVENTION

Therefore, with the foregoing in mind it is a primary object of the present invention to provide a new and improved construction of a gas sensing unit for use in environments containing explosive gases, which is not associated with the aforementioned shortcomings and limitations of the prior art proposals.

Another and more specific object of the present invention aims at eliminating the aforementioned drawbacks and, in particular, devising a gas sensing unit for use in environments containing explosive gases, which in conjunction with a central station forms a gas sensing signaling system, and which gas sensing unit contains a gas sensor or gas sensing element which, when exposed to the action of reduction gases, alters its electrical resistance, and further, wherein the gas sensor and evaluation circuit are assembled together in a single, explosion protected housing as the gas sensing unit.

A still further important object of the invention aims at providing a new and improved construction of a gas sensing unit, wherein it is possible to readily exchange the gas sensor or gas sensing element, without having to expose the evaluation circuit to the ambient atmosphere, and wherein additionally it is possible to carry out balancing of the gas sensors at the factory of the manufacturer.

Now in order to implement these and still further objects of the invention, which will become more readily apparent as the description proceeds, the invention contemplates that the gas sensing unit contains within a housing thereof at least two mutually separated spaces or chambers, of which the one, constituting a compression-proof chamber or space, contains the electronic evaluation circuit, and the second is designed as an explosion-protected chamber or space. This second chamber or space has a cover formed of a gas pervious sintered or powdered metal, through which there is possible the gas exchange with the ambient atmosphere or surroundings and which cover closes-off said second chamber or space. Further, the gas sensor or gas sensing element is provided with a balancing or compensation adapter.

According to a preferred embodiment the gas sensor together with the balancing adapter forms a unit. The adapter contains electrical circuit elements which are designed such that all gas sensor/adapter-units—notwithstanding the different properties of the individual gas sensors—always exhibit the same electrical characteristics (same relationship or ratio of the resistance of the gas sensor $R_G$ to the resistance of the adapter $R_A$, i.e. $R_G:R_A$=constant).

The gas sensor/balancing adapter-unit can be, for instance, designed such that the gas sensor and adapter cannot be disconnected from one another, or at best only with extreme difficulty. The gas sensor/adapter-unit possesses at its underside plug contacts or pins or equivalent structure, simultaneously serving for the mechanical connection with the housing and for the electrical connection with the evaluation circuit. Preferably, the plug connection device for the gas sensor-/adapter-unit is arranged in the cover which closes off the chamber or space containing the evaluation circuit.

This type of design enables dispensing with the need for balancing the gas sensor or gas sensing element at the site of erection or use. The adapter is balanced or tuned at the factory of the manufacturer to the gas sensor and is connected therewith into a unit or assembly. To control the sensitivity the gas sensor/adapter-units are exchanged and brought back to the factory, where checking, under controlled conditions, is easily possible. The gas sensing unit can remain at the erection site and the evaluation circuit, during the exchange operation, does not come into contact with the atmosphere.

According to a further preferred embodiment of the inventive gas sensing unit there is utilized as the gas sensor or gas sensing element a standard commercially available semiconductor gas sensor, which in the presence of oxidizable gases alters its electrical resistance. With these gas sensors it is possible to reliably detect, for instance, combustible gases within a concentration range of a few percent of the lower explosion limit (LEL). With these gas sensors or gas sensing elements it is possible to detect toxic and/or combustible gases contained in admixture with air, for instance methane, propane, butane, natural gas, cracked or product gas, hydrogen or carbon monoxide, but also vapors of organic liquids, such as for instance those of alcohols, ketones, esters, ethers; examples of vapors of toxic compounds are, among other things, toluene-2,4-diisocyanate (TDI), vinyl chloride and hydrogen sulfide. Also other oxidizable gases can be detected with such gas sensors, such as for instance ammonia.

One such type of gas sensor or gas sensing element can be, for instance, a solid state device, typically a semiconductor which, within a temperature range of 200° to 450° C., changes its resistance when exposed to the action of a reducing gas and which is coupled with an adapter, the resistance of which is chosen such that within the working temperature of the gas sensor the relationship or ratio of the resistance of the gas sensor to the resistance of the adapter is at a predetermined value. The resistance of the adapter can be, for instance, within a range of 50 to 270 ohms.

Instead of using the previously mentioned commercially available and known semiconductor-gas sensors it is also to use those which are commercially known as "pellistors", i.e. catalytic elements, also referred to commonly as "catalytic transducers", containing a short coil formed of platinum wire which is embedded in a pellet or sphere formed of a refractory oxide, for instance aluminum oxide. If an oxidizable gas comes into contact with the pellets, then such undergoes a combustion at its surface and additionally increases the temperature of the platinum wire, resulting in a change in the electrical resistance. This resistance change is evaluated in a balanced bridge circuit, for instance a Wheatstone bridge, and can serve for the concentration determination of oxidizable gases. If there are employed such pellistors, instead of the previously discussed semiconductor gas sensors or gas sensing elements, then the evaluation circuit can easily be accommodated to the altered electrical characteristics or properties of the pellistors.

According to a further preferred embodiment of the inventive gas sensing unit the cover or cover member of the second chamber or space, within which there is arranged the gas sensor/adapter-unit, is structured in the form of a substantially cylindrical, downwardly open bushing or sleeve, the walls and cover portion of which consists of a gas pervious sintered metal. This material is preferably chromium-nickel-molybdenum-sintered metal, especially having a filter fineness of about 30 $\mu$m.

To render possible a simple accommodation of the inventive gas sensing unit to different gases and/or concentration ranges, the gas sensing units preferably contain a switch for sensitivity setting. This switch can be switched through the application of a potential and is accessible without the need for opening the equipment with a special tool or the like.

The connection of the inventive gas sensing unit with the central station occurs by means of lines or cables, the connection of the lines with the gas sensing unit preferably being accomplished in a third, explosion-protected, threadable chamber or space within the housing of the gas sensing unit. The third chamber does not communicate with both of the other chambers or spaces.

In order to indicate which gas sensing unit has responded, a further preferred embodiment of the inventive gas sensing unit contains an explosion protected-response indicator, preferably directly at the chamber serving to receive the connection terminals.

In order to protect the cover member composed of sintered metal and provided for the chamber containing the gas sensor or gas sensing element, against the effects of spattered or spray water and dust, it is possible to equip the gas sensing unit with a splash-proof hood, preferably a metal hood having a gridded window or opening.

An appreciable advantage of the inventive gas sensing unit resides in the fact that it contains the evaluation circuit and gas sensing element or gas sensor within one gas sensing unit. Consequently, it is possible to assemble together into groups a multiplicity of gas sensing units, for instance up to ten gas sensing units per group, and to connect such to the central station. Hence, there is possible an appreciable simplification of the drawing of the lines or conductors, since, in this case, there is dispensed with the need for individual connections of each individual gas sensing unit by means of a multiplicity of lines with the central station as the same was necessary with the heretofore known gas sensing signaling systems. With the heretofore known gas sensing signaling systems or gas warning devices there were required for each gas sensing unit at least three lines for each individual gas sensor, which had to be guided to the region of the central station, whereas when using the inventive gas sensing unit there are required only a total of five lines per group of gas sensing units. This constitutes an appreciable simplification of the system design and wiring.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 2 which is composed of the FIGS 2a and 2b illustrates an inventive gas sensor/adapter-unit in separated condition, wherein FIG. 2a shows in perspective view from the lower side the gas sensor or gas sensing element and FIG. 2b illustrates in the same perspective showing the adapter, part of which has been rendered transparent for revealing internal structure;

FIGS. 3a, 3b, 3c, 3d and 3e illustrate respective circuit arrangements for the switch for sensitivity setting of the inventive gas sensing unit;

DETAILED DESCRIPTION OF THE PREFERRED EMBODIMENTS

Figure 1:
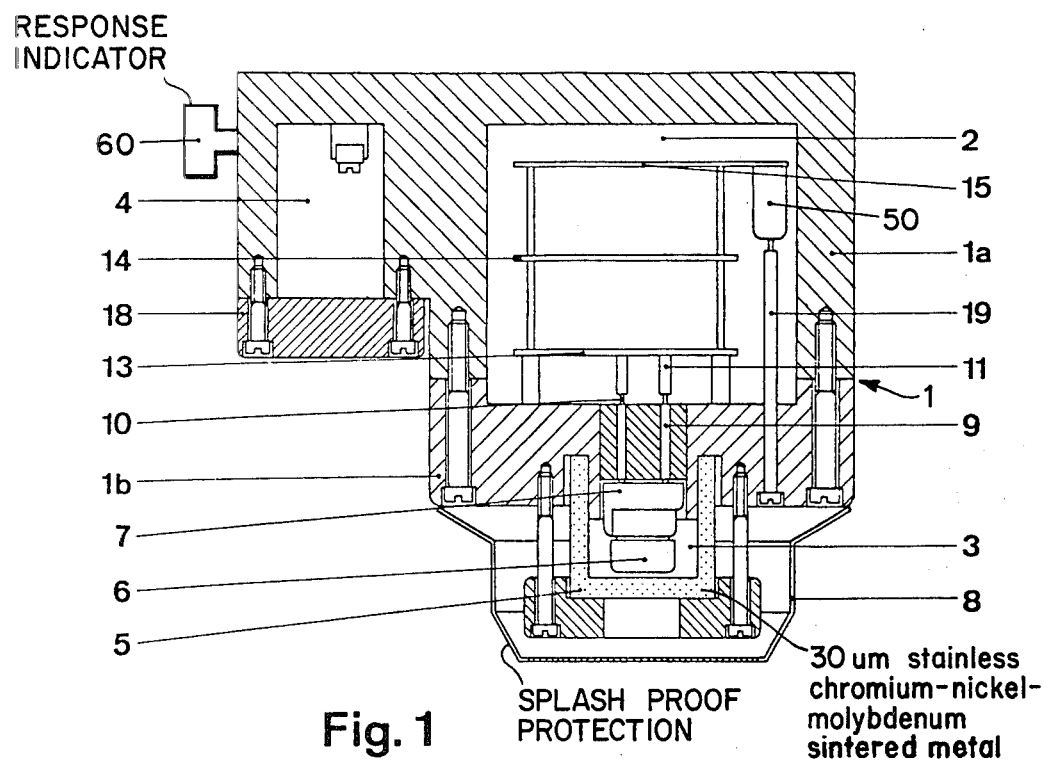
FIG. 1 is a schematic cross-sectional view of a gas sensing unit according to the invention.

Turning attention now to the drawings, it is first of all remarked that the gas sensing unit of the present development can be used in the gas sensing signaling system of the aforementioned commonly assigned, copending U.S. application Ser. No. 54,786, to which reference may be readily had and the disclosure of which is incorporated herein by reference. Therefore, in the disclosure to follow there will only be considered the specific features of the gas sensing unit of this development which constitute the subject matter of the invention and there have been omitted those portions of the system which are not absolutely necessary for one skilled in the art to readily understand the underlying principles and concepts of the present development. Directing attention to FIG. 1 there is illustrated therein the principle construction of an exemplary embodiment of inventive gas sensing unit which, as will be seen, contains three mutually separated, explosion protected or explosion secured chambers or spaces 2, 3 and 4. Within a housing 1 composed of a housing body member or body 1a and a cover member 1b, which housing is formed for instance of steel, aluminum or a suitable plastics material, there is arranged a first compression-proof chamber or space 2 within which there is located the evaluation circuit. This chamber or space 2 is conveniently referred to as the "circuit chamber or space".

Since the gas sensing unit is typically mounted in an inverted position, the cover or cover member 1b may be considered to close the chamber or space 2 towards its top and forms the base of the second chamber or space 3 which is structured so as to be explosion protected. The second chamber or space 3, conveniently referred to as the "sensor chamber or space", contains the gas sensor or gas sensing element 6 and the balancing adapter 7. This second chamber 3 communicates with the room or area which is to be monitored by means of the cover member or cover 5 which is formed of a gas pervious sintered metal as previously explained. Beneath the cover 5 there is arranged a splash-proof protection 8, for instance a metallic hood having a gridded window. Within the body member 1a of the housing 1 there is additionally arranged, as likewise previously explained, the third explosion protected chamber or space 4, conveniently referred to as the "connection chamber or space", containing the connection terminals or the like and hermetically sealed from the ambient air by the connection chamber-cover member or cover 18.

The sensor chamber or space 3 only contains the gas sensor or gas sensing element 6 and the balancing adapter 7, the construction of which has been more fully illustrated in FIGS. 2a and 2b. The gas sensor 6 possesses at its underside or lower surface contact pins 12, which when plugged together with the balancing adapter 7, engage into appropriate, not particularly shown bushings at the upper surface of the balancing adapter 7 and establish the mechanical and electrical connection between both of these parts or components 6 and 7.

According to a preferred embodiment the connection is accomplished by spring or resilient contacts such that separation of these components 6 and 7 is extremely difficult, if not totally impossible. In this way there is obtained the beneficial result that there can be effectively prevented any unauthorized disconnection of the balancing adapter 7 from the related gas sensor or gas sensing element 6 for whose balancing or compensation the same has been designed.

The balancing adapter 7 is provided at its underside with contact pins 17, by means of which the gas sensor-/adapter-unit can be plug connected into metallic bushings 9 located in the housing cover 1b and by virtue of which there is established the requisite mechanical connection with the housing 1, and, at the same time, the electrical connection with the evaluation circuit, the construction of which will be discussed more fully hereinafter. To this end the bushings or sockets 9, embedded by means of a suitable casting resin in the cover member 1b, are provided at the underside of the cover member 1b which is located within the chamber 2 with the contact pins 10 at which there is connected, by means of a socket or bushing plug 11 or equivalent structure, the evaluation circuit of the gas sensing unit.

Within the balancing adapter 7, shown particularly well in FIG. 2b, there is located a balancing resistance or resistor 16, by means of which it is possible to insure that all of the gas sensor/adapter-units 6, 7 have the same electrical characteristics. For this purpose the balancing resistor 16 is connected such that, upon assembly with the gas sensor or gas sensing element 6, there is formed a voltage divider, at the tap of which there can be tapped-off the signal which is infed to the evaluation circuit.

Figure 4:
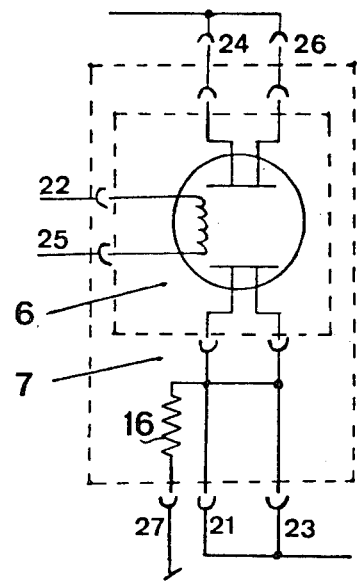
FIG. 4 shows the circuit arrangement of the gas sensor/adapter-unit.

The circuit configuration of the gas sensor/adapter-unit has been shown by way of example in FIG. 4. Between the terminals 24 and 26, which for safety reasons are designed as double plugs, and the terminal 27 there are dispositioned the gas sensor 6 and the balancing resistor or resistance 16. As mentioned, the gas sensor 6 and the balancing resistor 16 form a voltage divider, at the tap of which there can be tapped-off the signal which is infed to the evaluation circuit, by means of the plugs 21 and 23 also designed as a double plug arrangement for safety reasons. The resistance 16 is dimensioned such that the relationship or ratio of the balancing resistance 16 to the resistance of the gas sensor 6 is the same for all of the gas sensor/adapter-units. With the same supply voltage, in this case, the voltage at the terminals 21 and 23 is the same, with the same ambient conditions, for all of the gas sensor/adapter-units. The current infeed for the heating of the gas sensor 6 is accomplished by means of the terminals or connections 22 and 25.

As mentioned, within the compression-proof chamber or space 2 (FIG. 1) there is arranged the evaluation circuit. the latter is advantageously divided into a number of superimposed plates 13, 14 and 15 by way of example. The circuit elements are distributed upon the individual plates 13, 14 and 15 such that in the event of a possibly required change in the circuit design only as few as possible plates need be exchanged, preferably only a single plate. For instance, this may be necessary if the semiconductor gas sensor or gas sensing element is exchanged for a gas sensor operating according to the principle of catalytic oxidation, in which case there is required a balanced measuring bridge circuit in the evaluation circuit.

Remembering that the gas sensing unit is typically mounted in an inverted position, the plate 13 therefore will be referred to as the uppermost plate. This uppermost plate 13, the so-called inverter plate, has arranged thereon circuit components or elements which amplify the signal which is delivered by the gas sensing unit and renders such signal suitable for further conduction. Additionally, this plate 13 contains circuit elements in order to adjust, stabilize and monitor the sensor operating potential and the current needed for heating the gas sensor and for possibly generating a malfunction or disturbance indication signal. Upon interruption of the current, in the event of a shortcircuit or after a more or less depleted use of the equipment, a disturbance indication signal is transmitted to a corresponding signal line.

The intermediate plate 14, the so-called logic plate, contains circuit elements or components which are responsible for the evaluation of the sensor signal, for instance, the threshold value switch which delivers a warning signal and alarm signal or serves to further conduct a disturbance or malfunction signal. Additionally, there are also provided switching circuits which prevent the response of more than one gas sensing unit of the same group and additionally control suitable response indicators.

The lowermost plate 15, the so-called base plate, contains protective devices for the gas sensing unit, for instance protective devices against faulty connection, false poling, overvoltages and so forth, and, as the case may be, when necessary a switch 50 for changing the sensitivity of the gas sensing unit which can be serviced with a special tool, such as the belt-like connection or actuation element 19 shown in FIG. 1.

Figure 3E:
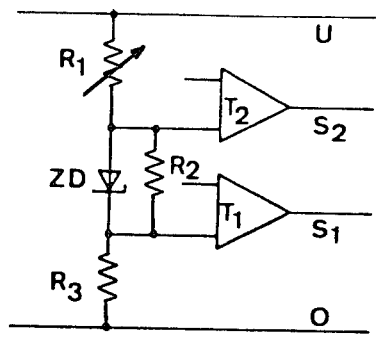

Gas sensing signaling systems are generally designed to operate as two-stage systems, i.e. at a certain gas concentration there is given a "warning", whereas at a higher gas concentration there is triggered an "alarm". In this respect attention is directed to the gas sensing signaling system disclosed in the aforementioned U.S. application Ser. No. 54,786. It is desirable that the threshold values for the "warning" and "alarm" modes of a gas sensing unit be accommodated to predestined fields of application. To this end there are provided setting or adjustment devices, as the same have been illustrated in FIGS. 3a to 3e. By means of these setting devices it is possible to simultaneously set or adjust both of the threshold values of a gas sensing unit. These setting or adjustment devices, contain, in each case, a voltage divider between the power supply line U and the ground bus O, which for the embodiment of FIG. 3a consists of three resistors or resistances $R_1$, $R_2$ and $R_3$, wherein the first resistance $R_1$ is adjustable. With the embodiment of FIG. 3b the resistance $R_2$ is replaced by a Zener diode ZD or, as shown in FIG. 3e, connected in parallel with a Zener diode ZD. In FIG. 3c a Zener diode ZD is connected in parallel to the resistance or resistor $R_3$. Both of the taps at the voltage divider are connected with the reference inputs of two threshold value switches $T_1$ and $T_2$, whose control inputs receive the analogue-output signal of the related gas sensing unit in accordance with the resistance change which arises under the action of the prevailing gas and whose outputs are connected with the signal lines $S_1$ and $S_2$. By adjusting the resistance $R_1$, with the embodiment of FIG. 3a, there is obtained a simultaneous proportional shifting of both concentration thresholds, whereas with the embodiments of FIGS. 3b and 3e there occurs a parallel shifting of both threshold values at least over one part of the adjustment range. With this combination it is possible to extensively compensate for non-linearity of the gas sensor elements. In the embodiment of FIG. 3c initially there are shifted both threshold values proportionally, until there is reached the breakdown voltage of the Zener diode. From this value on the lower threshold value remains constant, and specifically remains at the value which is governed by the Zener diode ZD. If, as shown in FIG. 3d, the Zener diode ZD is connected with the tap of a voltage divider formed of two resistances or resistors $R_3$ and $R_4$, i.e. if the resistance $R_3$ of the circuit configuration of FIG. 3c is divided into two components and the Zener diode is connected with the tap, and at least one of these components is adjustable, then it is possible to obtain a further, more sensitive setting possibility of the threshold value.

An important requirement which is placed upon gas sensing signaling systems is that such should be able to be accommodated as to their sensitivity to different conditions of use and that the set sensitivity not be accidentally changed or altered by non-authorized personnel. This safeguard is realized with the inventive gas sensing unit in that, the setting of the individual gas sensing units need not be accomplished, as was heretofore the case with the prior art gas warning devices, by adjusting a potentiometer at the erection site, rather such setting or adjustment can be accomplished by means of the above-discussed switch at the sensitivity stages which are fixedly prescribed by the manufacturer.

According to a preferred design there is provided at the equipment a switch, such as the switch 50 shown in FIG. 1, which can be actuated with the aid of a special actuation tool or key such as the previously described bolt-like actuation element 19 of FIG. 1, with the aid of which it is possible to set four different sensitivity stages of the gas sensing unit. It has been found that four sensitivity stages are usually satisfactory for conditions encountered in practice.

According to a further preferred embodiment of the inventive gas sensing unit there is mounted at the gas sensor housing or at the direct region of the gas sensing unit a response indicator, as generally indicated in FIG. 1 by reference character 60, which indicates in any suitable manner the momentary state of the gas sensing unit. Normally the warning stage can be indicated by a lamp which continuously illuminates, the alarm mode or state by continuous blinking of such lamp, and by means of the same response indicator it is also possible to indicate malfunction or disturbances of the response readiness of the gas sensing unit. This has the advantage that the occupants or personnel present in the monitored room or area are informed at all times about questionable or dangerous gas concentrations by the gas sensing unit.

Figure 5:
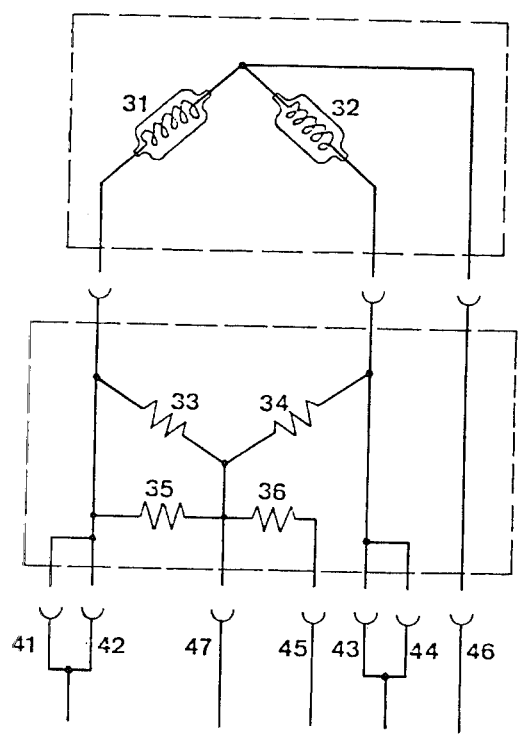
FIG. 5 shows a circuit arrangement of the gas sensor/adapter-unit where a catalytic sensor is used.

Finally, in FIG. 5 there is shown an exemplary circuit configuration of a catalytic sensor (pellistor)/adapter unit. Here a gas-active sensing element 31 and a gas-passive reference element 32 form one arm of a Wheatstone bridge. The other arm of this bridge consists mainly of resistors 33 and 34 which are located in the adapter unit 40. The Wheatstone bridge is powered (e.g. 20 V/500 mA) by means of terminals 41, 42 and 43, 44 which for good contact reasons are designed as double plugs. The output signal of the bridge is fed through terminals 45 and 46 to the evaluation circuit (e.g. differential amplifier input). A balancing resistor 35 is dimensioned such that with zero gas concentration, the output signal of the bridge will be zero. Similarly, resistor 36 is dimensioned such that for a given gas concentration, the output signal of the bridge circuit is the same for all pellistor/adapter units. Both resistors 35 and 36 can be evaluated in advance by means of contact plugs 41 (42), 47 and 45, 47, respectively.

Appreciable advantages of the inventive gas sensing unit reside in the fact that by housing the evaluation circuit in a chamber or space which is separated from the sensor within the gas sensing unit, there is realized an appreciably simpler construction of the entire gas sensing signaling system, an appreciably simpler design, maintenance and checking of the gas sensing unit, and there is possible an appreciably simpler setting and checking of the response preparedness or readiness of the gas sensing unit.

While there are shown and described present preferred embodiments of the invention, it is to be distinctly understood that the invention is not limited thereto, but may be otherwise variously embodied and practiced within the scope of the following claims. Accordingly,

What we claim is:

1. In a gas sensing unit for use in environments containing explosive gases and which in connection with a central station forms a gas sensing signaling system and which gas sensing unit contains a gas sensor which, in the presence of reducing gases, alters its electrical resistance, the improvement which comprises:
   housing means containing at least two separated chambers defining first and second chambers;
   said first chamber comprising a compression-proof chamber;
   electronic evaluation circuit means contained in said first compression-proof chamber;

said second chamber comprising an explosion protected chamber;

a cover member for closing said second chamber;

said cover member being formed of a gas pervious sintered metal rendering possible the exchange of gas with the surrounding atmosphere;

a balancing adapter provided for said gas sensor and contained within said second chamber;

said gas sensor and said balancing adapter collectively forming a gas sensor/adapter-unit;

said housing means including a cover for closing said first chamber; and said gas sensor/adapter-unit being pluggably arranged in said cover of said housing means.

2. The improvement as defined in claim 1, wherein:

said gas sensor comprises a semiconductor element whose resistance changes, when exposed to the action of a reducing gas, throughout a temperature range of 200° to 450° C.; and said balancing adapter containing a balancing resistance dimensioned such that the ratio of the resistance of the gas sensor to the resistance of the balancing resistance at the operating temperature of the semiconductor element and at a preselected gas concentration has a predetermined value.

3. The improvement as defined in claim 2, wherein:

said balancing resistance comprises an electrical resistance of approximately 50 to 270 ohms.

4. The improvement as defined in claim 1, wherein:

said gas sensor is structured to operate according to the principle of catalytic oxidation; and balanced bridge circuit means for evaluating the resistance changes of said gas sensor; and said balancing adapter containing balancing resistance means and constituting a pluggable balancing adapter for the balancing of the gas sensor and for the gain of the bridge circuit analogous to the gas sensor.

5. The improvement as defined in claim 1, wherein:

said cover member comprises a bushing formed of sintered metal;

said bushing surrounding said gas sensor; and said sintered metal of said bushing having a filter fineness of approximately 30 $\mu$m.

6. The improvement as defined in claim 5, wherein:

said sintered metal comprises stainless chromium-nickel-molybdenum sintered metal.

7. The improvement as defined in claim 1, further including:

switch means for setting the sensitivity of the gas sensing unit;

said switch means being accessible without opening the housing means and can be switched by applying a potential thereto and can be serviced with a special tool.

8. The improvement as defined in claim 1, wherein:

said housing means contains a further chamber defining a third chamber for the reception of connection terminals.

9. The improvement as defined in claim 8, further including:

explosion protected response indicator means.

10. The improvement as defined in claim 9, wherein:

said explosion protected response indicator means are mounted directly at the third chamber which receives the connection terminals.

11. The improvement as defined in claim 1, further including:

splash-proof protection means for protecting the gas sensing unit against dust contamination and clogging of the pores of the sintered metal.

12. The improvement as defined in claim 11, wherein:

said splash-proof protection means comprises a metallic hood having a gridded window.

* * * * *